(12) United States Patent
Wang et al.

(10) Patent No.: US 9,872,839 B2
(45) Date of Patent: *Jan. 23, 2018

(54) COMPOSITIONS AND METHODS FOR DIAGNOSING OR TREATING NEUTROPHIL-MEDIATED INFLAMMATORY DISEASE

(71) Applicant: The Board of Trustees of the University of Illinois, Urbana, IL (US)

(72) Inventors: Zhenjia Wang, Spokane, WA (US); Jaehyung Cho, Western Springs, IL (US); Asrar Malik, Hinsdale, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/425,528

(22) Filed: Feb. 6, 2017

(65) Prior Publication Data

US 2017/0143645 A1    May 25, 2017

Related U.S. Application Data

(63) Continuation of application No. 14/316,036, filed on Jun. 26, 2014, now Pat. No. 9,561,192.

(60) Provisional application No. 61/840,597, filed on Jun. 28, 2013.

(51) Int. Cl.
| | |
|---|---|
| A61K 31/05 | (2006.01) |
| A61K 9/16 | (2006.01) |
| G01N 33/543 | (2006.01) |
| G01N 33/50 | (2006.01) |
| A61K 9/51 | (2006.01) |
| A61K 31/573 | (2006.01) |
| A61K 9/00 | (2006.01) |

(52) U.S. Cl.
CPC ............ *A61K 31/05* (2013.01); *A61K 9/0019* (2013.01); *A61K 9/1658* (2013.01); *A61K 9/5169* (2013.01); *A61K 31/573* (2013.01); *G01N 33/5005* (2013.01); *G01N 2800/22* (2013.01)

(58) Field of Classification Search
None
See application file for complete search history.

(56) References Cited

U.S. PATENT DOCUMENTS 6,117,454 A * 9/2000 Kreuter ................ A61K 9/5138
424/489
9,561,192 B2 * 2/2017 Wang .................... A61K 9/5169

* cited by examiner

*Primary Examiner* — Abigail Vanhorn
(74) *Attorney, Agent, or Firm* — Valauskas Corder LLC (57) ABSTRACT

Disclosed are nanoparticle compositions comprising nanoparticles prepared from denatured, cross-linked albumin and a therapeutic agent for treating a neutrophil-mediated inflammation, and methods of treating neutrophil-mediated inflammation using the compositions.

13 Claims, 8 Drawing Sheets

COMPOSITIONS AND METHODS FOR DIAGNOSING OR TREATING NEUTROPHIL-MEDIATED INFLAMMATORY DISEASE

CROSS REFERENCE TO RELATED PATENTS

This application is a continuation application of U.S. patent application Ser. No. 14/316,036 filed Jun. 26, 2014, which claims the benefit of U.S. Provisional Application No. 61/840,597 filed Jun. 28, 2013, which is incorporated by reference in its entirety.

STATEMENT REGARDING GOVERNMENT SPONSORED RESEARCH OR DEVELOPMENT

This invention was made with government support under NIH P01 HL060678, R01 HL109439, and K25HL111157 awarded by National Institutes of Health. The government has certain rights in the invention.

FIELD OF THE INVENTION

The present invention relates generally to compositions and methods for diagnosing or treating neutrophil-mediated inflammatory disease.

BACKGROUND OF THE INVENTION

Neutrophil adhesion to activated endothelial cells and trans-endothelial migration of these cells are essential events of the innate immune response required for kill invading pathogens and bacterial clearance. While neutrophil recruitment into site of injury is the first-line of defense, excessive neutrophil infiltration and activation at the vessel wall is also the primary cause of inflammation and tissue damage. Neutrophils have been implicated in numerous inflammatory diseases such as acute lung injury, sepsis, and ischemia-reperfusion injury. Inhibition of $\beta2$ integrins using anti-$\beta2$ integrin antibodies has been shown to block adhesion of neutrophils to endothelial cells and prevent inflammation, leading to restored vascular integrity, which indicates that targeting neutrophils is a useful strategy in treating neutrophil-mediated inflammatory diseases. However, antibodies have the disadvantage of inducing generalized loss of neutrophil bactericidal function by impairing the ability of circulating neutrophils to adhere and migrate to the infected site.

Clearly, there is a demand for compositions and methods that permit targeting of activated neutrophils and treatment of neutrophil-mediated inflammatory diseases. The present invention satisfies this demand.

SUMMARY OF THE INVENTION

One object of certain embodiments of the present invention is to provide nanoparticle compositions and methods for detecting or treating neutrophil-mediated diseases.

In certain embodiments, the neutrophil-mediated disease is an inflammatory disease. In certain embodiments, the disease is a vascular inflammatory disease.

In certain embodiments, the compositions include nanoparticles prepared from denatured, cross-linked albumin. In certain embodiments, the albumin is denatured by desolvation. In certain embodiments, desolvation is performed using an alcohol. In certain embodiments, the alcohol is ethanol.

In certain embodiments, the albumin is cross-linked using glutaraldehyde.

In certain embodiments, the albumin nanoparticles have a mean particle diameter of about 100 nm±10 nm.

In certain embodiments, the nanoparticle composition includes a pharmaceutically acceptable excipient.

In certain embodiments, a therapeutic agent or a detectable moiety is incorporated within the nanoparticles or covalently conjugated to the surface of the nanoparticles.

In certain embodiments, the therapeutic agent is an anti-inflammation agent. In certain embodiments, the anti-inflammation agent is selected from anti-inflammatory glucocorticoids, NF-kB inhibitors, p38MAP kinase inhibitors, Syk/Zap kinase inhibitors, and siRNA oligonucleotides targeting a molecule in activated neutrophils, or any combination thereof.

In certain embodiments, the anti-inflammation agent is dexamethasone and/or piceatannol.

In certain embodiments, the detectable moiety is a fluorescent moiety or a chromogenic moiety.

In certain embodiments is provided a method of treating a neutrophil-mediated disease or condition in a subject in need of treatment by contacting activated neutrophils in the subject with a nanoparticle composition that contains nanoparticles prepared from denatured, cross-linked albumin and a therapeutic agent incorporated within or covalently attached to the nanoparticles.

In certain embodiments, the method involves treating a neutrophil-mediated inflammatory disease. In certain embodiments, the method involves contacting activated neutrophils with a nanoparticle composition comprising nanoparticles containing or conjugated to an anti-inflammation agent.

In certain embodiments, the method involves treating a neutrophil-mediated inflammatory disease selected from sepsis, myocardial infarction, acute lung injury, stroke and ischemia-reperfusion injury.

In certain embodiments is provided a method of detecting or monitoring neutrophil-mediated diseases comprising contacting neutrophils with a nanoparticle composition that contains nanoparticles prepared from denatured, cross-linked albumin and a detectable moiety incorporated within or covalently attached to the nanoparticles, and detecting uptake of the detectable moiety by activated neutrophils.

The present invention and its attributes and advantages will be further understood and appreciated with reference to the detailed description below of presently contemplated embodiments, taken in conjunction with the accompanying drawings.

BRIEF DESCRIPTION OF THE DRAWINGS

The preferred embodiments of the invention will be described in conjunction with the appended drawings provided to illustrate and not to the limit the invention, where like designations denote like elements, and in which.

DETAILED DESCRIPTION

Disclosed herein are nanoparticle compositions suitable for treating or detecting neutrophil-mediated diseases or conditions, including neutrophil-mediated inflammatory diseases. Nanoparticle compositions include denatured, cross-linked albumin and a therapeutic agent or a detectable moiety.

In certain embodiments, the nanoparticle compositions may include a pharmaceutically acceptable excipient, vehicle, or carrier.

"Treating" or "treatment" as used herein includes inhibiting a disease or disorder, i.e., arresting its development, relieving a disease or disorder, i.e., causing regression of the disorder; slowing progression of the disorder, and/or inhibiting, relieving, or slowing progression of one or more symptoms of the disease or disorder in a subject. Subjects treated may include human and non-human individuals, including warm blooded animals such as mammals afflicted with, or having the potential to be afflicted with one or more neutrophil-mediated diseases or disorders, including neutrophil-mediated inflammatory diseases.

In certain aspects, the disclosure provides a pharmaceutical composition comprising the nanoparticle of the disclosure together with one or more pharmaceutically acceptable excipients, carriers, or vehicles, and optionally other therapeutic and/or prophylactic components, as described in detail in U.S. Provisional Application No. 61/840,597.

An effective amount of a nanoparticle composition is an amount effective to provide the desired biological result. That result can be reduction and/or alleviation of the signs, symptoms, or causes of a disease, or any other desired alteration of a biological system. An appropriate "effective" amount in any individual case can be determined by one of ordinary skill in the art using routine experimentation.

In certain embodiments, nanoparticle compositions may be prepared as described below. In certain embodiments, the nanoparticles incorporate piceatannol, a spleen tyrosine kinase (Syk) inhibitor that blocks 'outside-in' β2 integrin signaling in leukocytes. Real-time intravital microscopy of inflamed post-capillary venules of live mice, the primary site of neutrophil adhesion and extravasation in the circulation, demonstrated that albumin nanoparticles are internalized by activated neutrophils through endocytosis that is in part mediated by Fcγ receptor III (FcγRIII). Mice treated with albumin nanoparticles incorporating piceatannol showed markedly reduced neutrophil adhesion and migration across the endothelium. A mouse model of endotoxin-induced acute lung injury mediated by the infiltration of neutrophils also showed that treatment with piceatannol-incorporated albumin nanoparticles prevents lung injury.

In certain embodiments, stable albumin nanoparticles were prepared by desolvation of albumin, for example, using ethanol, followed by albumin cross-linking using a cross-linking agent such as glutaraldehyde. As one of skill in the art will appreciate, any suitable albumin may be used in the practice of the invention, including, but not limited to, BSA, human serum albumin and ovalbumin. Any suitable cross-linking agent may be used to crosslink the albumin. To study internalization properties of albumin nanoparticles by phagocytes, fluorescent dyes were incorporated into nanoparticles. Transmission electron microscopy and dynamic light scattering demonstrated that the size of albumin nanoparticles with and without fluorescent dyes was similar, with a mean diameter of 100±10 (SD) nm. It is envisioned that albumin nanoparticle preparations having a particle diameter in the range of 50 nm to 300 nm may also be used in the practice of the invention.

Real-time fluorescence intravital microscopy was used to study the uptake of albumin nanoparticles by neutrophils. Vascular inflammation was induced by intrascrotal injection of the pro-inflammatory cytokine tumour necrosis factor (TNF-α) in mice. At 3 hr post-TNF-α challenge, cremaster muscle was exposed, and neutrophils adherent to activated venular endothelial cells were monitored. Intravenous injection of Cy5-loaded albumin nanoparticles resulted in the nanoparticles being largely internalized by the leukocytes adherent to the inflamed venular endothelial cells, and to some extent by neutrophils slowly rolling along the vessel wall. However, nanoparticles were not internalized by the TNF-α activated endothelium itself. To confirm that the nanoparticles were primarily internalized by neutrophils, an Alexa Fluor 488-labeled anti-mouse Gr-1 antibody and Cy5-loaded albumin nanoparticles were simultaneously infused. Anti-mouse Gr-1 antibody and albumin nanoparticles showed marked co-staining. In control experiments, non-immune isotype control antibody, IgG did not show a signal. To address whether albumin nanoparticles can also be internalized by unstimulated neutrophils in the circulation, Cy5-loaded albumin nanoparticles were infused intravenously. Unstimulated neutrophils did not take up Cy5-loaded albumin nanoparticles, indicating that only adherent neutrophils were able to internalize the nanoparticles. Nanoparticle internalization by adherent monocytes, another phagocytic cell involved in inflammation, was evaluated. Adherent monocytes, unlike neutrophils, did not internalize albumin nanoparticles.

To investigate determinants of nanoparticle internalization, uptake of three different types of nanoparticles by activated neutrophils were compared. In the first two, BSA nanoparticles were made by ethanol-induced albumin desolvation to denature albumin, followed by albumin cross-linking to form stable particles. Albumin nanoparticles were then either incorporated with fluorescent dye (Cy5-loaded albumin nanoparticles) or chemically conjugated to Alexa Fluor 647 by carboxyl-amine reaction that forms covalent bonds between Alexa Fluor 647 and albumin nanoparticles (Alexa Fluor 647-conjugated albumin nanoparticles). Additionally, albumin-conjugated polystyrene nanoparticles were prepared by coating yellow-green fluorescence polystyrene nanoparticles having a diameter of 100 nm with native BSA. Uptake of these two types of albumin nanoparticles by Gr-1 positive neutrophils following intravenous infusion at 3 hr after intrascrotal injection of TNF-α was compared. Alexa Fluor 647-conjugated albumin nanoparticles were found to be internalized by the adherent neutrophils and showed characteristic punctual distribution in the cytosol, whereas Cy5-loaded albumin nanoparticles showed diffuse fluorescence throughout the cell. The latter observation was attributed to the release of Cy5 dye bound non-covalently to nanoparticles following nanoparticle internalization. The punctual structures in the cytosol represented individual or aggregated nanoparticles, presumably into lyso-endosomal compartments. Conjugation of Cy5 to albumin nanoparticles also exhibited the same punctual structures in adherent neutrophils as Alexa Fluor 647-conjugated albumin nanoparticles; thus, dye conjugation method prevents dye dispersal following nanoparticle internalization. Based on a comparison of the fluorescence intensities of internalized Cy5-loaded nanoparticles with Cy5-conjugated nanoparticles, uptake efficiency of two types of albumin nanoparticles was found to be similar. Further, the general morphology of the adherent neutrophils internalizing either type of nanoparticle was found to be the same, and cells had similar surface area of 54±6 (mean±SD) µm². Unlike nanoparticles made from denatured albumin, native albumin-conjugated polystyrene nanoparticles remained bound to the surface of neutrophils without being internalized. Native albumin conjugated to Cy5 was not taken up by neutrophils. As quantified by multiple images, 95% of all adherent neutrophils similarly internalized either dye-loaded or dye-conjugated albumin nanoparticles. In contrast, neither albumin-conjugated polystyrene particles nor Cy5-conjugated albumin was internalized by the adherent neutrophils.

Because FcγRs activate endocytosis by binding IgG-opsonized particles and denatured proteins, whether nanoparticles made of denatured albumin could be internalized through FcγR signaling was evaluated Neutrophils obtaining from FcγRIII$^{-/-}$ mice exhibited significantly reduced uptake of albumin nanoparticles compared to wild-type (WT). By measuring fluorescence intensity of Cy5-loaded albumin nanoparticles per neutrophil, a distribution of nanoparticle uptake per neutrophil was obtained. Based on this, FcγRIII was found to contribute to ~50% of total uptake of albumin nanoparticles, consistent with the role of FcγR signaling as a mechanism of immune complex internalization by neutrophils. The basis of residual uptake is unclear but may involve other Fcγ receptors. Macrophage antigen-1 (Mac-1 or αMβ2 integrin) and lymphocyte function-associated antigen-1 (LFA-1 or αLβ2 integrin) mediate neutrophil adhesion during vascular inflammation and denatured albumin binds to Mac-1 and may contribute to uptake of denatured proteins; however, deletion of Mac-1 and LFA-1 had no effect on uptake of albumin nanoparticles.

Albumin nanoparticles loaded with piceatannol, a Syk inhibitor, were evaluated for the ability to reverse TNF-α-mediated firm adhesion of neutrophils to venular endothelial cells, and thus mitigate inflammation. Syk signaling is crucial in the mechanism of 'outside-in' integrin signaling that mediates β2 integrin-dependent neutrophil adhesion, spreading, and migration. Piceatannol selectively inhibits Syk activity but because of low solubility in water, has not been effective as an anti-inflammatory agent. Intravenous infusion of piceatannol-loaded albumin nanoparticles, 1 mg/kg body weight of piceatannol (50 µM), significantly reduced the number of adherent neutrophil and concomitantly increased the number of rolling cells. In controls, albumin nanoparticles alone had no effect.

To investigate further the mechanisms of action of piceatannol-loaded albumin nanoparticles, a flow chamber assay was used in which mouse neutrophils interacted with a monolayer of TNF-α-activated mouse lung endothelial cells under shear condition. In control experiments, Cy5-loaded albumin nanoparticles were internalized by Gr-1 positive neutrophils as in mouse venular studies above. The nanoparticle signal was slightly increased in neutrophils stimulated with N-formyl-methionyl-leucyl phenylalanine (fMLF). However, treatment of neutrophils with piceatannol-loaded albumin nanoparticles, 800 µg/ml (200 µM as piceatannol) under shear conditions markedly reduced β2 integrin-mediated neutrophil spreading and migration across TNF-α-activated endothelial cells and inhibited neutrophil adhesion. Thus, piceatannol-loaded albumin nanoparticles functioned by inhibiting β2 integrin-mediated 'outside-in' signaling through Syk signaling, consistent with the known function of Syk. Syk phosphorylation in fMLF-stimulated neutrophils was also abrogated in neutrophils internalizing piceatannol-loaded albumin nanoparticles indicating that the drug loaded into nanoparticles blocked Syk activity. A 3-(4,5-Dimethylthiazol-2-yl)-2,5-diphenyl tetrazolium bromide (MTT) assay was performed to eliminate any possible drug toxicity effect. Incubating neutrophils with piceatannol-loaded albumin nanoparticles, 800 µg/ml (200 µM as piceatannol), did not affect cell viability. Thus, piceatannol-loaded albumin nanoparticles inhibited Syk phosphorylation, thereby impairing β2 integrin-mediated 'outside-in' signaling required for neutrophil spreading and migration.

Excessive accumulation of neutrophils in lungs is a major factor in the pathogenesis of acute lung injury associated with sepsis. β2 integrin-dependent neutrophil adhesion to lung endothelial cells contributes to acute lung injury. Therefore, piceatannol-loaded albumin nanoparticles were evaluated for the ability to ameliorate lung neutrophil infiltration induced by intraperitoneal injection of lipopolysaccharide (LPS, 10 mg/kg body weight). Treating mice with piceatannol-loaded albumin nanoparticles, 4.3 mg/kg body weight as piceatannol (200 µM in blood), 2 hr after LPS challenge, markedly reduced lung tissue myeloperoxidase (MPO) activity, an indication of reduced neutrophil sequestration. Infiltration of both neutrophils and monocytes determined by bronchoalveolar lavage (BAL) was also reduced by treating mice with piceatannol-loaded albumin nanoparticles (4.3 mg/kg body weight as piceatannol). Comparison of MPO activity in LPS-induced lung inflammation after administration of piceatannol-loaded albumin nanoparticles and piceatannol (free drug) alone also showed that piceatannol-loaded nanoparticles were far more efficacious than piceatannol alone. Because albumin nanoparticles are preferentially internalized by neutrophils in vivo, inhibition of neutrophil infiltration in lungs by piceatannol-loaded albumin nanoparticles appears to contribute to reduced monocyte infiltration. These results also showed the utility of albumin nanoparticle loading of piceatannol for the treatment of acute lung injury.

In summary, an albumin nanoparticle approach for the delivery of drugs into inflammatory neutrophils adherent to endothelial cells has been developed that is in part dependent on FcγRIII signaling. Adhesion of neutrophils to activated endothelial cells was required for the internalization of albumin nanoparticles. Because FcγRs are highly expressed in adherent neutrophils during inflammation and vascular diseases, nanoparticles made of denatured albumin can be used to target inflammatory neutrophils while sparing the essential host-defense function of circulating neutrophil. This strategy limits the undesirable effects of globally blocking the essential bactericidal function of neutrophils.

Further, the results reported herein demonstrate the feasibility of using albumin nanoparticles to target activated neutrophils without conjugating ligands or antibodies to the nanoparticle surface. The results hence provide the proof-of-concept of a novel nanoparticle-based therapeutic approach for targeting activated neutrophils to treat a range of inflammatory disorders. This represents a departure from the approach typically taken for delivering therapeutics to desired cells, based on coating of ligands and antibodies to the nanoparticle surface.

Methods

Preparation of Albumin Nanoparticles Loaded with Fluorescent Dyes or Piceatannol.

Bovine serum albumin (BSA) nanoparticles were prepared by the desolvation technique (Weber et al., Int. J. Pharm. 196, 197-200 (2000), which is incorporated by reference herein). BSA was first dissolved at a concentration of 20 mg/ml in deionized water. Nanoparticles were made by continuous addition to 1 ml of BSA (20 mg/ml) of 3.5 ml of ethanol under stirring (650 rpm) for 10 min at RT. In some experiments, 1 ml BSA (20 mg/ml) was mixed and incubated with 40 μl of Cy5 dye (5 mg/ml) in chloroform for 1 hr, followed by desolvation with ethanol. To make piceatannol-loaded albumin nanoparticles, 1 ml of 20 mg/ml of BSA solution was incubated with 1 mg of piceatannol dissolved in DMSO for 1 hr. To form stable albumin nanoparticles with or without a dye or piceatannol, BSA molecules were cross-linked by adding 20 μl of 0.2% glutaraldehyde in the suspension. The suspension was stirred overnight at RT. Nanoparticle suspension was centrifuged at 14,000 rpm for 20 min at 4° C. After drying albumin nanoparticles, 80-90% albumin was obtained to form the nanoparticles. The nanoparticle pellet was re-suspended in water or phosphate-buffered saline, pH 7.4 for the study.

To measure the efficiency of piceatannol incorporation in BSA nanoparticles, different concentrations of piceatannol were added in the initial albumin solution. After centrifugation of suspension of piceatannol-loaded BSA nanoparticles at 14,000 rpm at 4° C. for 30 min, the supernatant (containing unbound piceatannol) was collected and centrifuged using Microcon (10-kD cut-off) to separate unbound piceatannol from free BSA molecules. Piceatannol molecules were quantified by measuring the absorbance at 328 nm. The loading yield of piceatannol in albumin nanoparticles was calculated by the following equation: Loading yield (%)=(Drug used−unloaded drug)/Drug used. After drying and weighting piceatannol-loaded albumin nanoparticles, 10-14wt % of piceatannol was loaded in albumin nanoparticles.

To conjugate covalently Alexa Fluor-647 or Cy5 dye to albumin nanoparticles, carboxyl-amine reaction between dye and albumin was used. After albumin nanoparticles were made using the desolvation method as described above, Alex Fluor 647-NHS was mixed with albumin nanoparticles, and incubated the mixture for 2 hr at RT. Albumin nanoparticles were centrifuged to remove free dye molecules to obtain Alexa Fluor 647-conjugated albumin nanoparticles.

Real-Time Fluorescence Intravital Microscopy.

In vivo intravital microscopy was performed as described[13]. TNF-α (0.5 μg in 250 μl saline) was intrascrotally injected into wild-type (WT) or knockout mice. At 3 hr after TNF-α injection, mice were anesthetized with intraperitoneal injection of the mixture of ketamine (80 mg/kg), xylazine (2 mg/kg), and acepromazine (2 mg/kg) and maintained at 37° C. on a thermo-controlled rodent blanket and a tracheal tube was inserted. After excision of the scrotum, cremaster muscles were exteriorized on the intravital microscope table. The cremaster preparation was superfused with thermo-controlled (37° C.) and aerated (95% $N_2$, 5% $CO_2$) bicarbonate-buffered saline during the experiment. Fluorescently-labeled albumin nanoparticles (100 μg) in 100 μl of saline were infused through a cannula placed in a jugular vein, followed by infusion of the Alexa Fluor 488-labeled anti-mouse Gr-1 antibody (0.05 μg/g body weight). Rolling and adherent neutrophils were monitored in an area of 0.02 $mm^2$ in inflamed cremaster muscle venules. Images were recorded using an Olympus BX61W microscope with a 60×/1.0 NA water immersion objective lens and a high speed camera (Hamamatsu C9300) connected to an intensifier (Video Scope International). To study the therapeutic effects of piceatannol-loaded albumin nanoparticles, the Alexa Fluor 488-labeled anti-mouse Gr-1 antibody was intravenously infused, followed by infusion of either piceatannol-loaded albumin nanoparticles or control albumin nanoparticles (150 μg of albumin nanoparticles containing 50 μM piceatannol). At 30 or 60 minutes after infusion of nanoparticles, rolling and adherent neutrophils were monitored. In some experiments, an Alexa Fluor 488-labeled anti-mouse F4/80 antibody (2 μg/mouse) was infused to monitor monocytes. Neutrophils that remained stationary or did not exceed displacement of>8 μm for at least 30 sec were considered adherent. To quantify neutrophil rolling and adherence, each vessel was monitored for>3 min. Approximately 20 venules from 3 mice were monitored for each group of experiments. Data analysis was performed using Slidebook 5.5 (Intelligent Imaging Innovations). To quantify fluorescence signals, fluorescence intensities of albumin nanoparticles internalized into neutrophils were integrated using the software, and the distribution of nanoparticle uptake in neutrophils was analyzed.

Statistical Analysis.

Data are expressed as mean±SD or SEM. Data were analyzed using one-way ANOVA (multiple groups) or Student t-test (two groups) of Origin 8.5, with p values <0.05 were considered significant.

Results

Uptake of Albumin Nanoparticles by Adherent Neutrophils in Venules.

Figure 1:
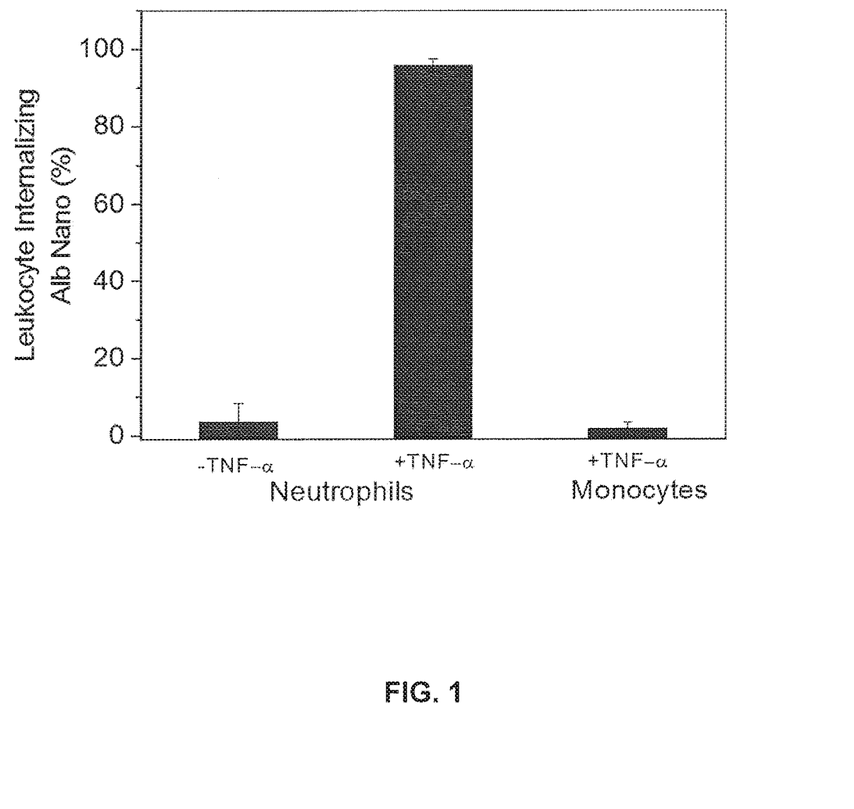
FIG. 1 is a graph showing the percentage of neutrophils and monocytes treated or untreated with TNF-α that internalized albumin nanoparticles.

Intravital microscopy of mouse cremaster muscle venules demonstrated that Cy5-loaded albumin nanoparticles are internalized by activated neutrophils following administration of TNF-α (0.5 μg/mouse) and during surgical stress-induced vascular inflammation. Neutrophils were visualized by intravenous infusion of Alexa Fluor 488 anti-mouse Gr-1 antibody. In the TNF-α challenge group, the nanoparticles were intravenously infused 3 hr post-intrascrotal injection of TNF-α (0.5 μg/mouse). Monocytes were visualized by infusion of Alexa Fluor 488 anti-mouse F4/80 antibody 3 hr after infusion of TNF-α. FIG. 1 shows the percentage of neutrophils and monocytes internalizing albumin nanoparticles. In all experiments, 100 μg fluorescent dye-labeled albumin nanoparticles/mouse was infused intravenously. All data represent mean±SEM (n=13-20 vessels in 3 mice per group).

Characteristics of Internalization Properties of Different Types of Albumin Nanoparticles.

Figure 2:
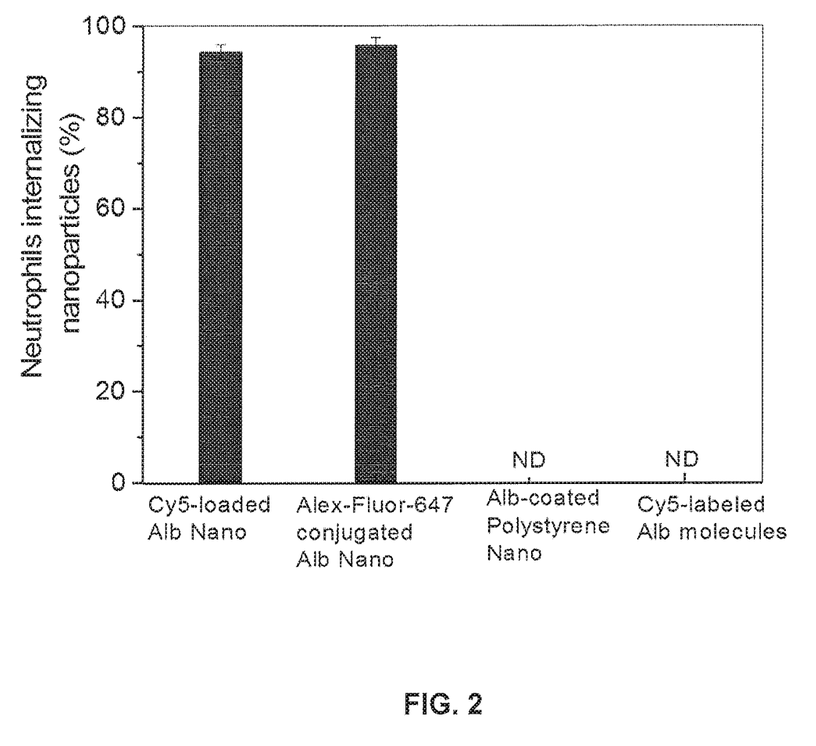
FIG. 2 is a graph showing the percentage of neutrophils internalizing various types of nanoparticles or Cy5-labeled native albumin.

Three different formulations of fluorescently-labeled albumin nanoparticles were studied. Albumin nanoparticles made from denatured albumin were either loaded with Cy5 to form dye-loaded Alb nanoparticles or the albumin nanoparticle surface was chemically conjugated with Alex Fluor 647 or Cy5 to form dye-conjugated Alb nanoparticles, as described above. The third nanoparticle formulation was prepared by conjugating native (undenatured) albumin to polystyrene nanoparticles having a diameter of 100 nm. Intravital microscopy was performed in mice as above. Dye-loaded and dye-conjugated albumin nanoparticles were internalized by Gr-1-positive neutrophils. Native albumin-conjugated polystyrene nanoparticles were bound to the neutrophil surface, and not internalized. Cy5-conjugated native albumin was not internalized by Gr-1-positive neutrophils. With reference to FIG. 2, quantitative analysis of percentage of Gr-1-positive neutrophils internalizing the three types of nanoparticles and Cy5-labeled native albumin shows that both dye-loaded Alb nanoparticles and dye-conjugated Alb nanoparticles were internalized by Gr-1-positive neutrophils, whereas native albumin conjugated polystyrene nanoparticles and Cy5-labeled native albumin were not internalized by Gr-1-positive neutrophils. Results are shown as mean±SEM (n=13-20 vessels in 3 mice per group). ND=not detected.

Contribution of FcγRIII Mechanism in Mediating Albumin Nanoparticle Internalization.

Figure 3:
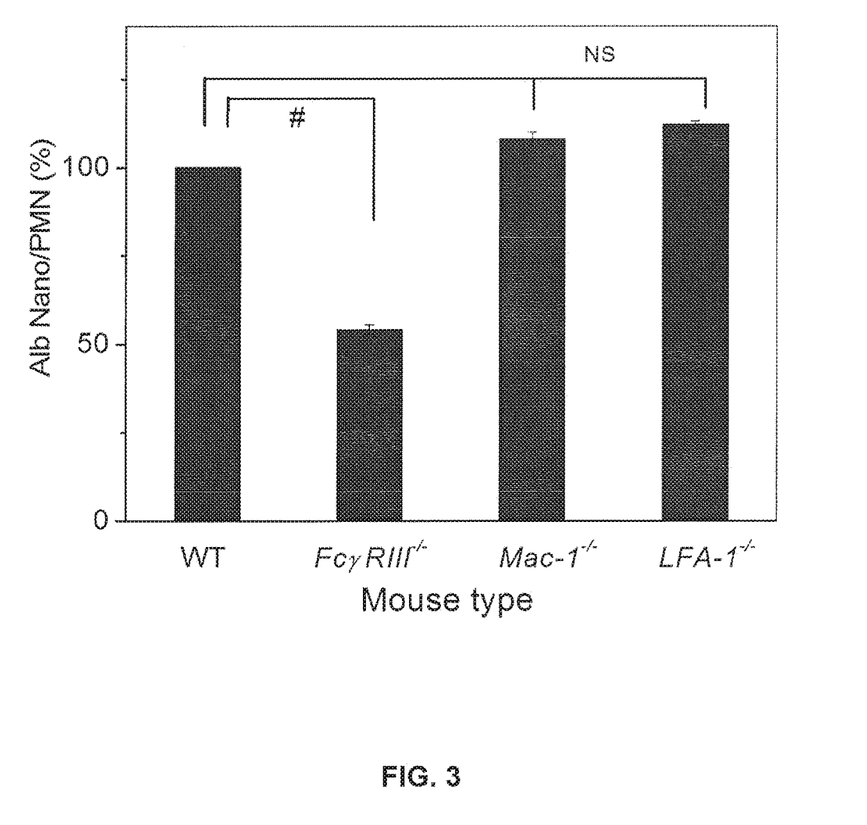
FIG. 3 is a graph showing uptake of albumin nanoparticles by wild-type, FcγRIII$^{-/-}$, Mac-1$^{-/-}$, and LFA-1$^{-/-}$ mice.

Intravital microscopy of cremaster muscle inflamed venules was performed in wild-type (WT) and FcγRIII$^{-/-}$, Mac-1$^{-/-}$, and LFA-$^{-/-}$ mice. Cy5-loaded albumin nanoparticles were intravenously infused 3 hr after intrascrotal injection of TNF-α (0.5 μg/mouse). Histograms of Cy5-loaded albumin nanoparticles internalized by neutrophils (more than 500 neutrophils in 3 mice per group) in WT and FcγRIII$^{-/-}$ mice showed greater internalization of Cy5-loaded albumin nanoparticles by WT neutrophils than by FcγRIII$^{-/-}$ neutrophils, indicating a role for FcγRIII in internalization of the albumin nanopoarticles. Similar experiments performed using Mac-1$^{-/-}$ and LFA-1$^{-/-}$ mice indicated that Mac-1 and LFA-1 do not play a role in internalization of the albumin nanoparticles. FIG. 3 shows the percentage of albumin nanoparticle uptake by polymorphonuclear neutrophils (PMNs) in WT versus knockout mice in each group. P<0.0001 vs. WT mice after ANOVA and Dunnett's test. NS, not significant.

Therapeutic Activity of Albumin Nanoparticles in Vascular Inflammation and Lung Injury Models.

Figure 4A:
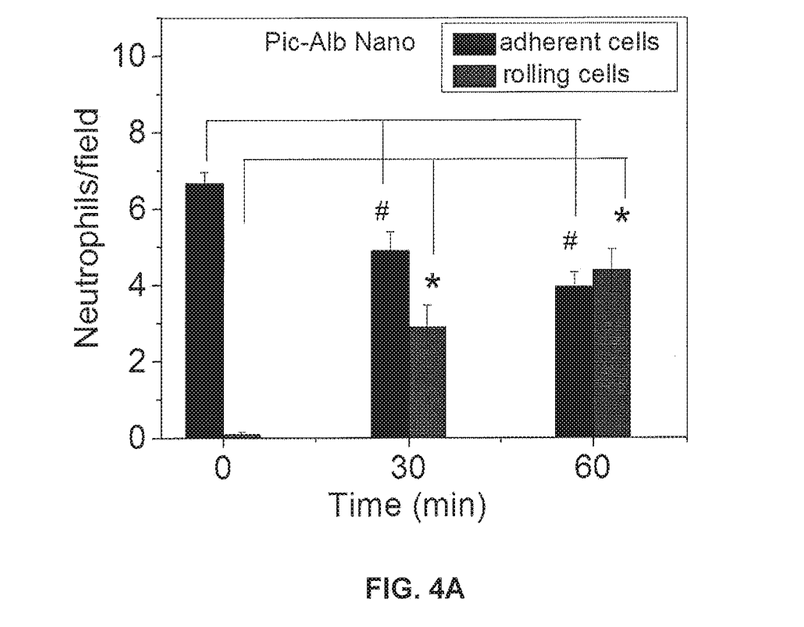
FIG. 4 is a graph showing adherent and rolling neutrophils/field as a function of time in mice treated with albumin nanoparticles with (FIG. 4A) and without (FIG. 4B) piceatannol.
Figure 4B:
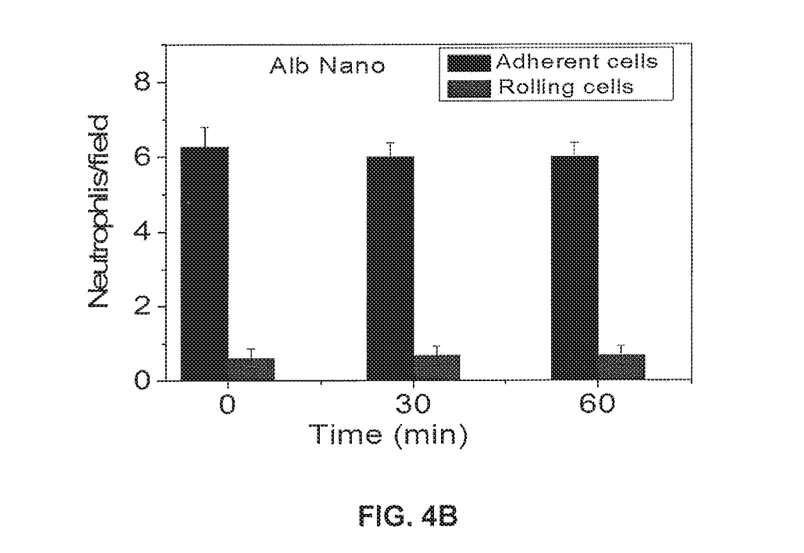

Intravital microscopy performed on mice intravenously infused with Alexa Fluor 488-conjugated antibodies before and at 1 hr post-intravenous infusion of piceatannol-loaded albumin nanoparticles (50 μM piceatannol) showed rolling and adhesion of neutrophils. Quantification of neutrophil adhesion and rolling in FIG. 4 is graph showing the number of adherent and rolling neutrophils per field in TNF-α-activated cremaster muscle vessels at baseline and at 30 and 60 min after intravenous infusion of piceatannol-loaded albumin nanoparticles (FIG. 4A) or albumin nanoparticles (FIG. 4B).

Figure 5:
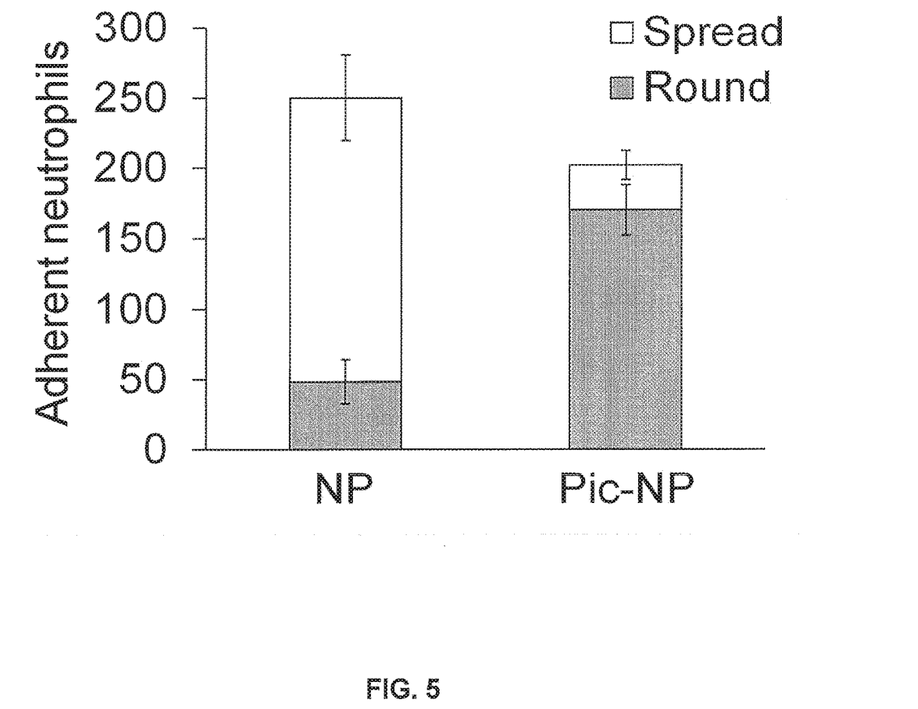
FIG. 5 is a graph showing round and spread adherent neutrophils treated with albumin nanoparticles or albumin nanoparticles incorporating piceatannol.

FIG. 5 shows the results of an assay of mouse neutrophils pre-treated with 800 μg/ml albumin nanoparticles (NP) or piceatannol-loaded albumin nanoparticles (Pic-NP, 200 μM as piceatannol), and stimulated with N-formyl-methionyl-leucyl-phenylalanine (fMLF). Flow chamber assay at fixed shear representing venous shear (1 dyne/cm$^2$) was performed as described in The number of adherent neutrophils (either spread or round) was quantified during the 10-min recording period. Data represent mean±SD (n=3).

Figure 6:
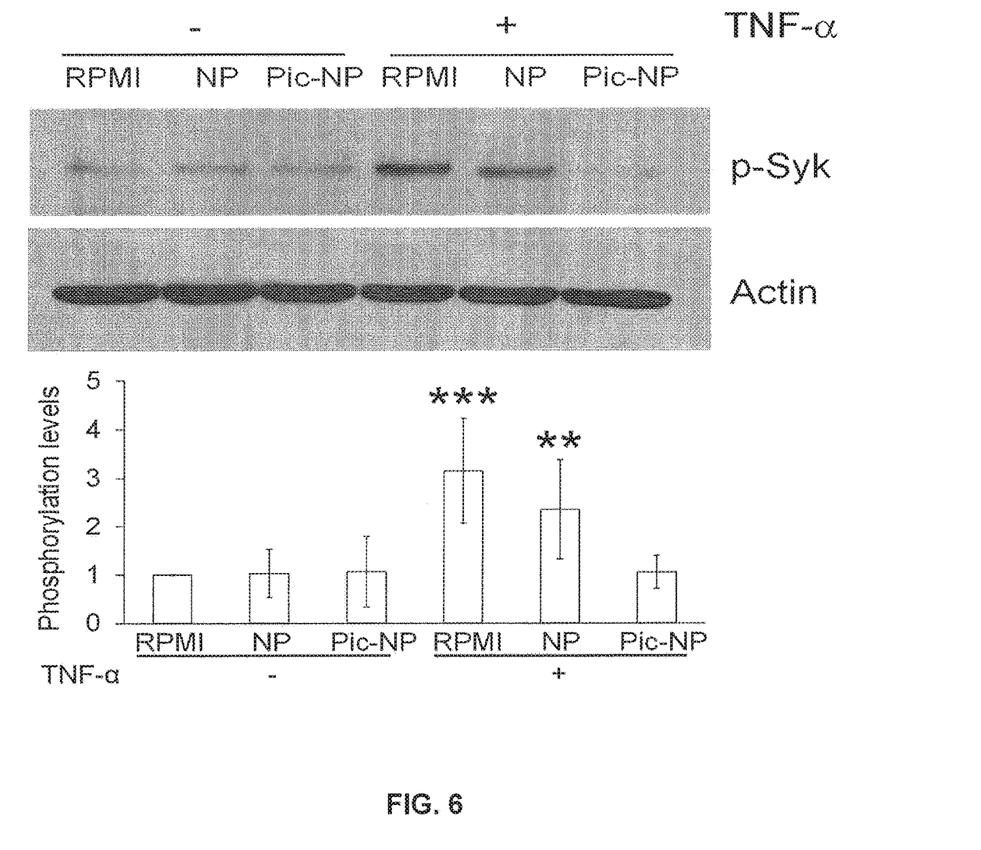
FIG. 6 is an immunoblot and graph showing phosphorylation of Syk in lysates of unstimulated neutrophils and neutrophils stimulated with TNF-α and treated with albumin nanoparticles or albumin nanoparticles incorporating piceatannol.

Mouse neutrophils were plated on fibrinogen-coated surfaces and incubated with RPMI culture media, 800 μg/ml albumin nanoparticles (NP) or piceatannol-loaded albumin nanoparticles (Pic-NP, 200 μM) in the presence or absence of 50 ng/ml TNF-α for 30 min. Cell lysates were immunoblotted with anti-phospho Syk-Tyr525/526 antibody (FIG. 6). The results show that piceatannol inhibited phosphorylation of Syk in TNF-α stimulated neutrophils. Data represent mean±SD (n=3). P<0.01 and *P<0.001 vs. unstimulated cells after ANOVA and Dunnett's test.

Unstimulated or fMLF-stimulated mouse neutrophils were treated with 800 μg/ml albumin nanoparticles (NP) or piceatannol-loaded albumin nanoparticles (Pic-NP, 200 μM as piceatannol) for 1 hr. MTT assay was performed as described in Methods. Cell viability is presented as mean±SD (n=3). **P<0.01 vs. unstimulated cells after ANOVA and Dunnett's test. Cell viability was not different among any experimental group.

Figure 7:
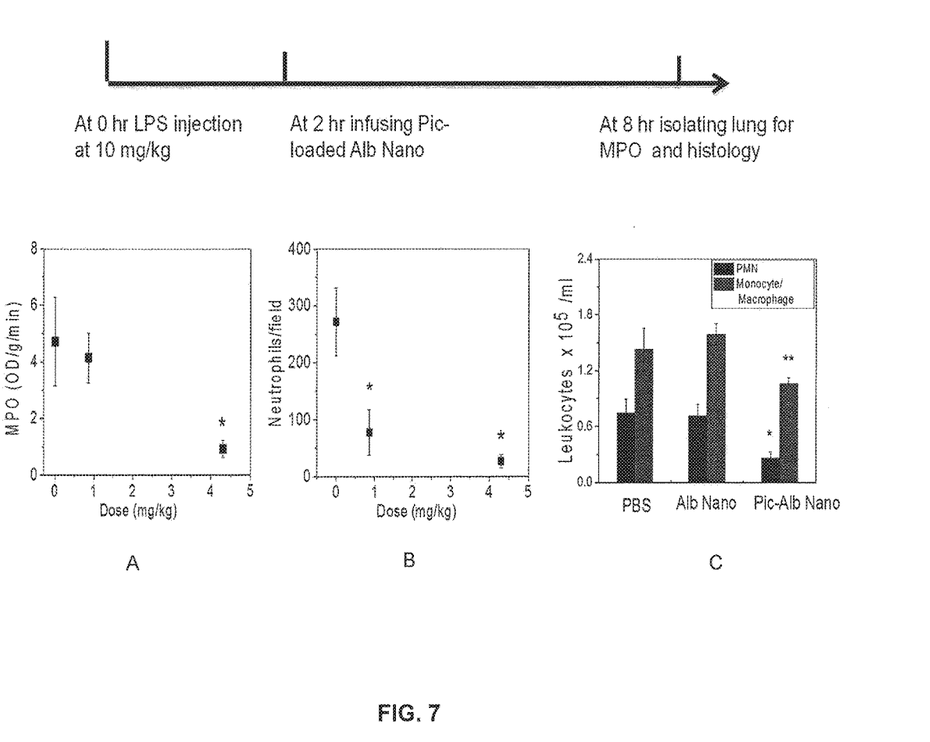
FIG. 7A is a graph of lung myeloproxidase (MPO) activity in lungs of mice with LPS-induced acute lung inflammation before and after intravenous infusion of piceatannol-loaded albumin nanoparticles.
FIG. 7B is a graph of the number of neutrophils sequestered in lungs of mice with LPS-induced acute lung inflammation before and after intravenous infusion of piceatannol-loaded albumin nanoparticles.
FIG. 7C shows the concentration of leukocytes in bronchoalveolar lavage (BAL) after intravenous infusion of albumin nanoparticles (Alb-Nano) or piceatannol-loaded albumin nanoparticles (Pic-Alb Nano).
Figure 8:
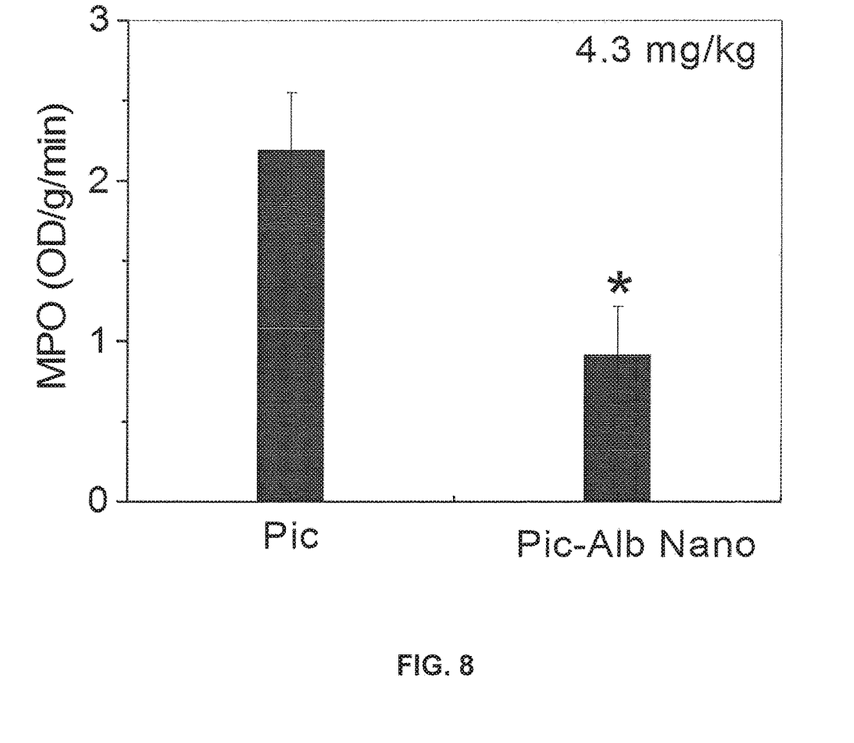
FIG. 8 is a graph of lung myeloproxidase (MPO) activity in lungs of mice with LPS-induced acute lung inflammation treated with piceatannol alone or piceatannol-loaded albumin nanoparticles.

Effects of piceatannol-loaded albumin nanoparticles on LPS-induced lung inflammation were evaluated. With reference to FIG. 7, the line above the FIG. 7A-C describes the protocol. Lung myeloproxidase (MPO) activity (FIG. 7A) and number of neutrophils sequestered in lungs (FIG. 7B) before and after intravenous infusion of piceatannol-loaded albumin nanoparticles is shown. Data represent mean±SD (n=3). *P<0.001 vs control after ANOVA. FIG. 7C shows the concentration of leukocytes in bronchoalveolar lavage (BAL) after intravenous infusion of albumin nanoparticles (Alb-Nano) or piceatannol-loaded albumin nanoparticles (Pic-Alb Nano) at a piceatannol doses of at 4.3 mg/kg body weight. *P<0.01 and **P<0.05. FIG. 8 compares the efficacy of intravenous infusion of piceatannol (Pic)-loaded albumin nanoparticles compared to free piceatannol, at a dose of 4.3 mg/kg body weight, in reducing neutrophil infiltration in LPS-induced acute lung inflammation, as assessed by MPO activity. *P<0.05 vs. free piceatannol after Student t-test.

While the disclosure is susceptible to various modifications and alternative forms, specific exemplary embodiments of the present invention have been shown by way of example in the drawings and have been described in detail. It should be understood, however, that there is no intent to limit the disclosure to the particular embodiments disclosed, but on the contrary, the intention is to cover all modifications, equivalents, and alternatives falling within the scope of the disclosure as defined by the appended claims.

We claim:

1. A method of treating a neutrophil-mediated inflammatory disease in a subject in need of treatment comprising:
   administering to the subject a therapeutically effective amount of a composition comprising nanoparticles, each nanoparticle consisting of denatured, cross-linked albumin and a therapeutic agent, the nanoparticles selectively binding to and internalized by activated neutrophils.

2. The method of claim 1, wherein the therapeutic agent is one or more selected from the group consisting of anti-inflammatory glucocorticoids, NF-kB inhibitors, p38MAP kinase inhibitors, Syk/Zap kinase inhibitors and siRNA oligonucleotides.

3. The method of claim 1, wherein the therapeutic agent is dexamethasone or piceatannol.

4. The method of claim 1, wherein the neutrophil-mediated inflammatory disease is selected from the group consisting of sepsis, myocardial infarction, acute lung injury, stroke and ischemia-reperfusion injury.

5. The method of claim 1, wherein the therapeutic agent is loaded within the nanoparticles or covalently conjugated to the albumin.

6. The method of claim 1, wherein each of the nanoparticles has a mean particle diameter of about 90 nm to about 110 nm.

7. The method of claim 1, wherein the nanoparticles are administered intravenously.

8. The method of claim 1, wherein the subject is a human.

9. The method of claim 1 wherein the denatured albumin is denatured by desolvation.

10. The method of claim 9 wherein the albumin is desolvated by treatment with ethanol.

11. The method of claim 1 wherein the albumin is bovine serum albumin.

12. The method of claim 1 wherein the albumin is cross-linked with glutaraldehyde.

13. A composition comprising nanoparticles, each nanoparticle consisting of denatured, cross-linked albumin and a therapeutic agent, the nanoparticles selectively binding to and internalized by activated neutrophils.

* * * * *